(12) United States Patent
Akita et al.

(10) Patent No.: US 7,306,336 B2
(45) Date of Patent: Dec. 11, 2007

(54) FUNDUS OBSERVATION APPARATUS (75) Inventors: Junichi Akita, Nukata-gun (JP);
Akihiro Fujishiro, Toyohashi (JP);
Toshifumi Sumiya, Nukata-gun (JP);
Naoyuki Kondo, Anjo (JP)

(73) Assignee: Nidek Co., Ltd., Gamagori (JP)

( * ) Notice: Subject to any disclaimer, the term of this patent is extended or adjusted under 35 U.S.C. 154(b) by 356 days.

(21) Appl. No.: 11/018,505

(22) Filed: Dec. 22, 2004

(65) Prior Publication Data
US 2005/0157259 A1 Jul. 21, 2005

(30) Foreign Application Priority Data
Dec. 26, 2003 (JP) ............................. 2003-431762

(51) Int. Cl.
*A61B 3/14* (2006.01)
(52) U.S. Cl. ..................... 351/206; 351/205; 351/207; 351/208; 351/246
(58) Field of Classification Search ........ 351/205–209, 351/213, 221, 246
See application file for complete search history.

(56) References Cited

U.S. PATENT DOCUMENTS 5,565,938 A * 10/1996 Hanamura et al. .......... 351/206

6,099,127 A * 8/2000 Manivannan et al. ....... 351/221

FOREIGN PATENT DOCUMENTS

| JP | A 05-137696 | 6/1993 |
| JP | A 07-178056 | 7/1995 |

* cited by examiner

Primary Examiner—Scott J. Sugarman
Assistant Examiner—James R Greece
(74) Attorney, Agent, or Firm—Oliff & Berridge, PLC (57) ABSTRACT An apparatus for observing a fundus of an eye of an examinee has an observation optical system having an image-pickup element which obtains a time-series fundus image, a display part which displays the obtained fundus image on its monitor as a moving image, a determination part which determines a standard fundus image based on the displayed image, a memory part which stores the determined image, a calculation part which digitizes the image based on a threshold luminance level to obtain a digitized image thereof, digitizes a present fundus image obtained after the determination of the standard image based on the threshold luminance level to obtain a digitized image thereof and compares the obtained digitized images two-dimensionally to obtain their positional difference, and a display control part for correcting a display position of the present fundus image based on the obtained positional difference to display the corrected image on the monitor.

4 Claims, 7 Drawing Sheets

FUNDUS OBSERVATION APPARATUS

BACKGROUND OF THE INVENTION

1. Field of the Invention

The present invention relates to a fundus observation apparatus for observing a fundus of an eye of an examinee.

2. Description of Related Art

Conventionally, there is an apparatus such as a fundus camera and a perimeter, which picks up a fundus image of an eye of an examinee and displays the fundus image to be observable on a monitor. For this kind of apparatus, there is an apparatus which displays the fundus image picked up in a time series as a moving image on the monitor. The eye, however, is moved by eyeball's vibrations, movement of a line of sight, or the like, so that the fundus image on the monitor is unintentionally moved accordingly. Consequently, it is difficult to perform observation, examination, measurement, diagnosis or the like, with high precision.

SUMMARY OF THE INVENTION

An object of the invention is to overcome the problems described above and to provide a fundus observation apparatus capable of displaying a fundus image as a moving image favorably on a monitor.

To achieve the objects and in accordance with the purpose of the present invention, an apparatus for observing a fundus of an eye of an examinee, the apparatus is provided with an observation optical system having an image-pickup element which obtains a fundus image in a time series, a display part having a monitor which displays the obtained fundus image on the monitor as a moving image, a determination part which determines a standard fundus image based on the displayed fundus image, a memory part which stores the determined standard fundus image, a calculation part which digitizes the standard fundus image based on a threshold luminance level to obtain a digitized standard fundus image, digitizes a present fundus image which is obtained after the determination of the standard fundus image based on the threshold luminance level to obtain a digitized present fundus image and compares the obtained digitized present fundus image with the obtained digitized standard fundus image two-dimensionally to obtain a positional difference therebetween, and a display control part which controls to correct a display position of the present fundus image based on the obtained positional difference to display the corrected present fundus image on the monitor.

In another aspect of the present invention, an apparatus for observing a fundus of an eye of an examinee, the apparatus is provided with an exit unit which emits three-color laser beams in red, green and blue independently, a scanning unit which scans the emitted respective beams two-dimensionally on the fundus, an image-obtaining part which obtains respective fundus images by photo-receiving respective reflection beams from the fundus independently, a display part having a monitor which displays the obtained fundus images on the monitor as a moving image, a calculation part which digitizes the obtained respective fundus images based on a threshold luminance level to obtain respective digitized fundus images and compares the obtained respective digitized fundus images two-dimensionally to obtain positional differences among them, and a display control part which controls to align the respective fundus images based on the obtained positional differences and superimpose the respective fundus images to be displayed as a composite fundus image on the monitor.

Additional objects and advantages of the invention are set forth in the description which follows, are obvious from the description, or may be learned by practicing the invention. The objects and advantages of the invention may be realized and attained by the ophthalmic apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
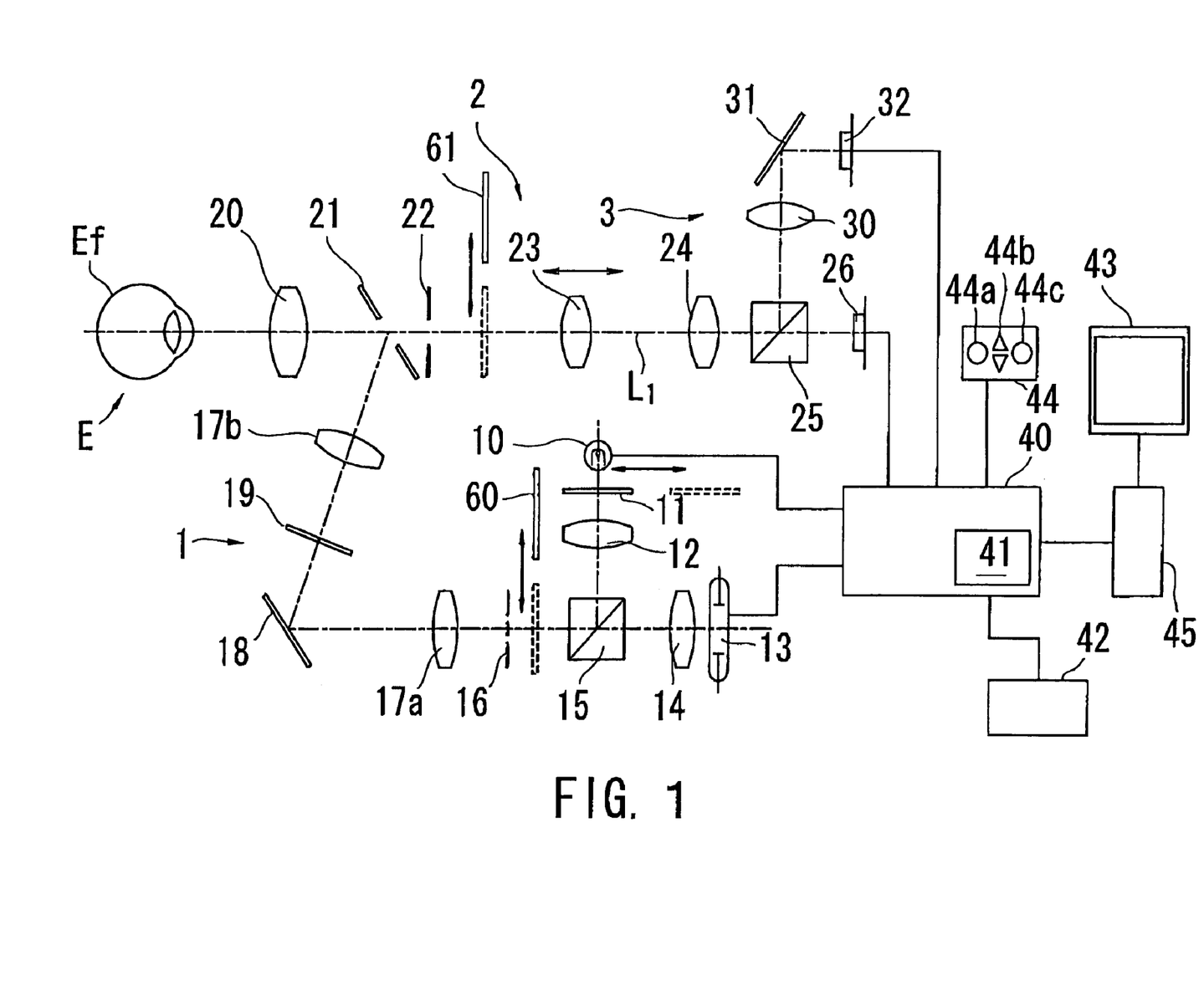
FIG. 1 is a view showing a schematic configuration of an optical system and a control system of a fundus camera consistent with the present invention.

A detailed description of one preferred embodiment of a fundus observation apparatus embodied by the present invention is provided below with reference to the accompanying drawings. FIG. 1 is a view showing a schematic configuration of an optical system and a control system of a fundus camera capable of fluorescent observation and fluorescent photographing in addition to ordinary infrared observation and visible photographing, being a type of an apparatus for observing a fundus, which is consistent with the preferred embodiment of the present invention. The optical system includes an illumination optical system 1, a fluorescent observation and photographing optical system 2 and an infrared observation optical system 3.

Illumination Optical System 1

Visible to infrared illumination light emitted from an illumination light source 10 for observation such as a halogen light is projected onto a ring slit plate 16 via a condenser lens 12 and a half mirror 15 to illuminate the slit plate 16. Also, visible illumination light emitted from an illumination light source 13 for photographing such as a flash light is projected onto the slit plate 16 via a condenser lens 14 and the mirror 15 to illuminate the slit plate 16. The mirror 15 makes the illumination light for observation coaxial with the illumination light for photographing.

An infrared transmission filter 11, having a property of transmitting light within the infrared range, is removed from an optical path only at the time of the fluorescent observation and the fluorescent photographing, and inserted in the optical path at the other time than the fluorescent observation and the fluorescent photographing.

The illumination light passing through a ring slit in the slit plate 16 and formed into a ring shape, passes through a relay lens 17*a*, a reflection mirror 18, a black dot plate 19 having a black dot at its center and a relay lens 17*b*, and are reflected on a peripheral surface of an opening of an apertured mirror 21. Then, the reflected illumination light is converged once in the vicinity of a pupil of an eye E of an examinee by an objective lens 20 and is diffused to be projected onto a fundus Ef of the eye E, and illuminates the fundus Ef uniformly.

An excitation filter 60, having a property of transmitting light with wavelengths of about 400 nm to about 520 nm (blue), is inserted in an optical path between the mirror 15 and the slit plate 16 only at the time of the fluorescent observation and the fluorescent photographing and removed from the optical path at the other time than the fluorescent observation and the fluorescent photographing.

<Fluorescent Observation and Photographing optical System 2>

Visible reflection light from the fundus Ef passes through the lens 20, the opening of the mirror 21, a photographing diaphragm 22, a focusing lens 23 and an image forming lens 24 to enter a dichroic mirror 25. The diaphragm 22 is arranged at a position approximately conjugate with the pupil of the eye E with respect to the lens 20. The lens 23 is arranged movable by a moving mechanism consisting of a motor and the like in a direction of an optical axis L1. The mirror 25 has a property of reflecting light within the infrared range and transmitting light within the visible range. The visible reflection light transmitted through the mirror 25 is photo-received on a CCD camera 26 for fluorescent observation and photographing having sensitivity to the visible range to form an image of the fundus Ef on its image-pickup surface.

A barrier filter 61, having a property of transmitting light with wavelengths of about 520 nm or more, is inserted in an optical path between the diaphragm 22 and the lens 23 only at the time of the fluorescent observation and the fluorescent photographing and removed from the optical path at the other time than the fluorescent observation and the fluorescent photographing.

<Infrared Observation Optical System 3>

Infrared reflection light from the fundus Ef passes through the lens 20 to the lens 24 to enter the mirror 25. The infrared reflection light reflected by the mirror 25 passes through a relay lens 30 and a reflection mirror 31, and is photo-received on a CCD camera 32 for infrared observation having sensitivity to the infrared range to form an image of the fundus Ef on its image-pickup surface.

<Control System>

Into a calculation and control unit 40 which performs driving-control of the entire fundus camera and the like, inputted are image signals outputted from the cameras 26 and 32. The calculation and control unit 40 including a plurality of CPUs and the like for image processing is capable of parallel-processing the inputted image signals. The calculation and control unit 40 is connected with a monitor 43 via a display control part 45.

A memory 41 is for temporarily storing (capturing) a standard fundus image and a present fundus image described later. A memory 42 is for storing (capturing) the photographed fundus image. A switch part 44 having a switch 44*a* for determining the standard fundus image, switches 44*b* for changing a threshhold luminance level for digitizing the obtained fundus image, a switch 44*c* for switching operation modes of the apparatus, and the like, is provided on a periphery of an unillustrated operation unit of the present fundus camera.

Figure 2:
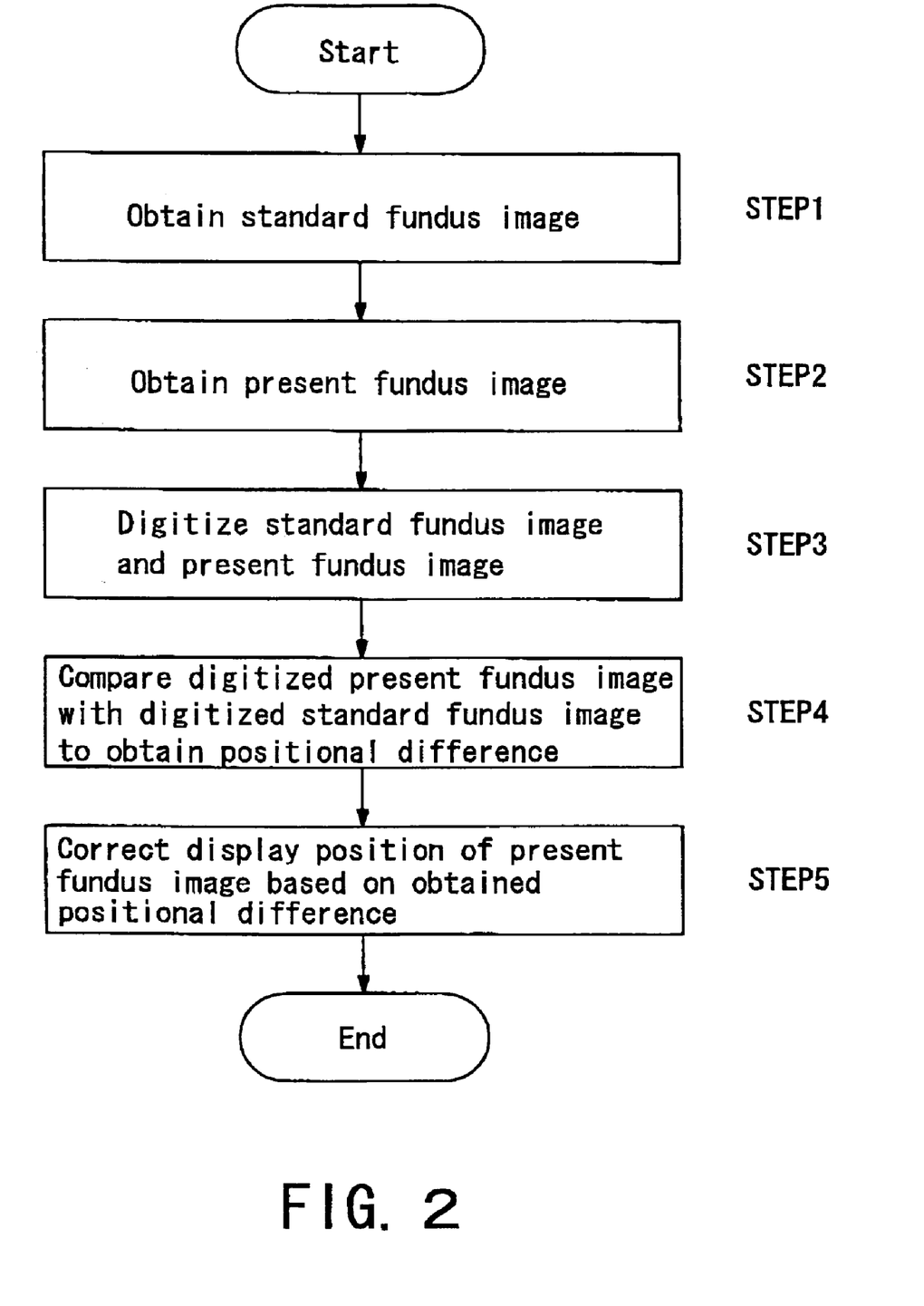
FIG. 2 is a flow chart showing how to display a fundus image for observation.

Next, in the fundus camera having a constitution above, how to display the fundus image for observation on the monitor 43 is described referring to a flow chart in FIG. 2. Besides, in the present embodiment, a case will be described as an example where the fluorescent observation of the fundus image is performed.

Mydriastics are put in the eye E, and a fluorescer (fluorescein sodium) is injected into a vein. When the pupil of the eye E is dilated enough and the fluorescer starts to circulate in blood vessels of the fundus (a retina), alignment is performed through operation of the operation unit such as a joystick so that the present fundus camera has a predetermined positional relationship with respect to the eye E.

And, when the operation mode of the apparatus is switched to a fluorescent-observation and fluorescent-photographing mode based on an operation signal from the switch 44*c*, the calculation and control unit 40 controls to insert the filter 60 and the filter 61 in the optical paths and remove the filter 11 from the optical path using unillustrated driving means. At the same time, the calculation and control unit 40 controls to display the fundus image picked up by the camera 26 on the monitor 43.

The illumination light from the light source 10 is made into blue illumination light for fluorescence excitation by the filter 60 to be projected onto the fundus Ef. In the fundus Ef, the fluorescer circulating in the blood vessels is excited by the blue illumination light to produce a fluorescence of a band beyond 520 nm. The fluorescence is photo-received on the camera 26 via the lens 20 to the mirror 25 (including the filter 61), and the fundus image picked up by the camera 26 is displayed on the monitor 43.

Figure 3A:
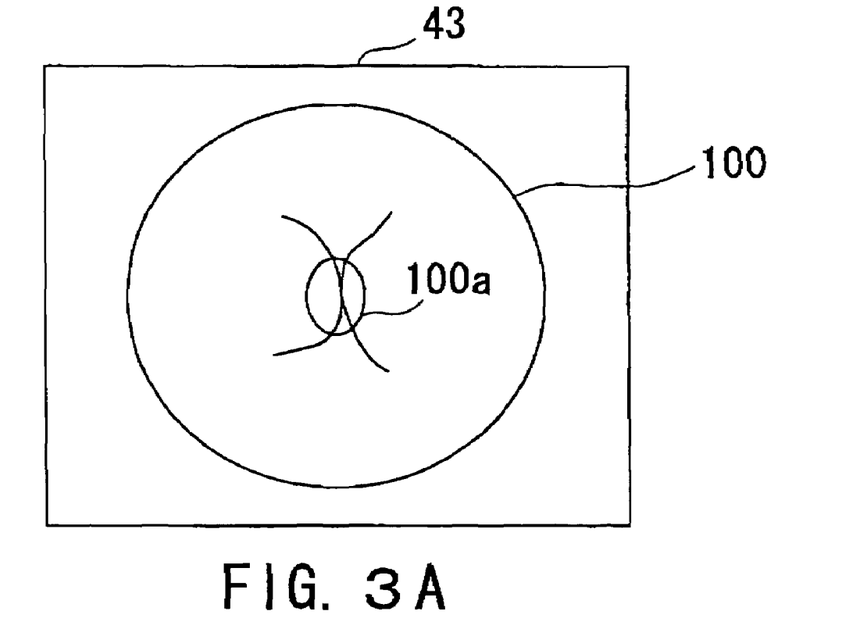
FIGS. 3A and 3B are views showing examples of the fundus image displayed on a monitor.
Figure 3B:
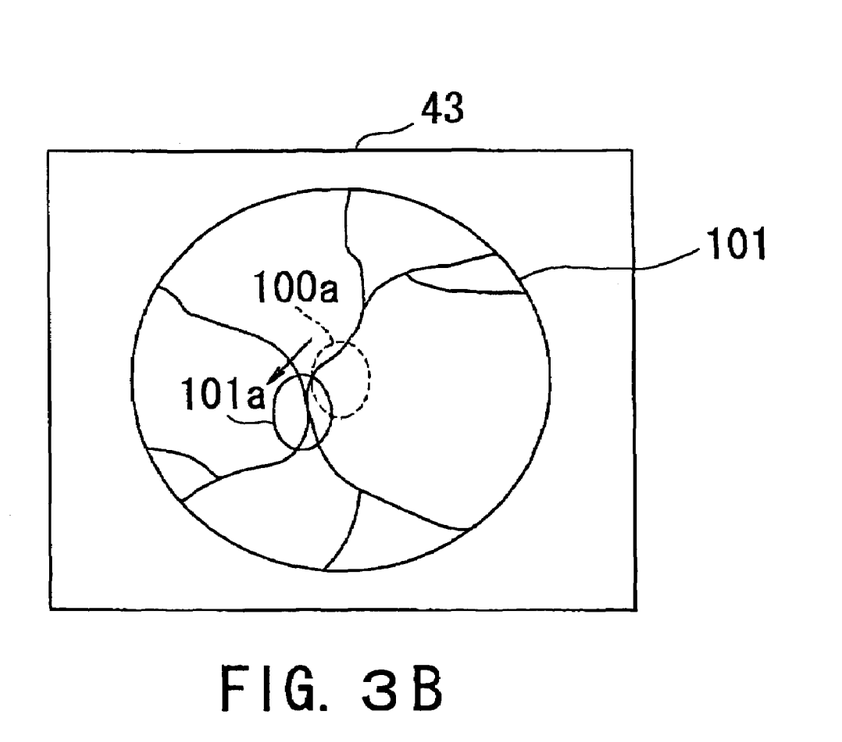

After that, the fundus camera is slightly moved through further operation of the operation unit, and when a display position of a fundus image 100 displayed on the monitor 43 is brought in a desired position as shown in FIG. 3A (here, the fundus camera is aligned so that an optic papilla 100*a* is placed at the center of the monitor 43), the fundus image 100 displayed on the monitor 43 is stored (captured) in the memory 41 as the standard fundus image by the calculation and control unit 40 based on an operation signal from the switch 44*a* (STEP 1).

When the standard fundus image is obtained, a fundus image which is to be picked up thereafter by the camera 26 is stored (captured) by frame successively in a time series as the present fundus image in the memory 41 by the calculation and control unit 40 (STEP 2).

Figure 4A:
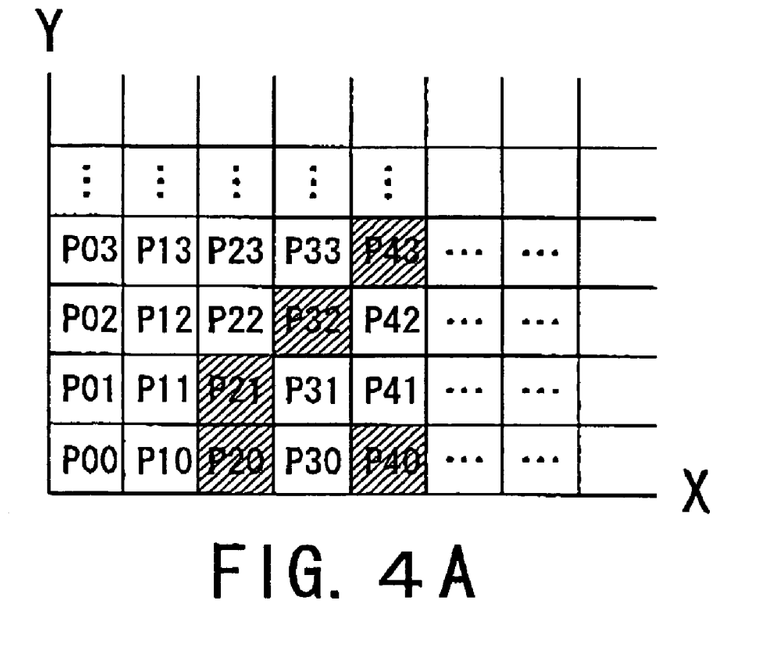
FIGS. 4A and 4B are frame formats showing an example of the fundus image pixel by pixel.

Next, the calculation and control unit 40 controls to digitize the standard fundus image and the present fundus image stored (captured) in the memory 41 based on a predetermined threshhold luminance level (STEP 3). Here, FIG. 4A is a frame format showing a part of the fundus image pixel by pixel. Besides, P00, P10, P20 and the like indicate addresses of respective pixels of the fundus image displayed on the monitor 43, and shaded pixels (e.g., P20, P40 and the like) indicate that luminance thereof is sufficiently higher than the other pixels. Besides, FIG. 5 is a schematic diagram representing luminance in one pixel row (P00, P10, P20, P30, P40 . . . ).

Figure 4B:
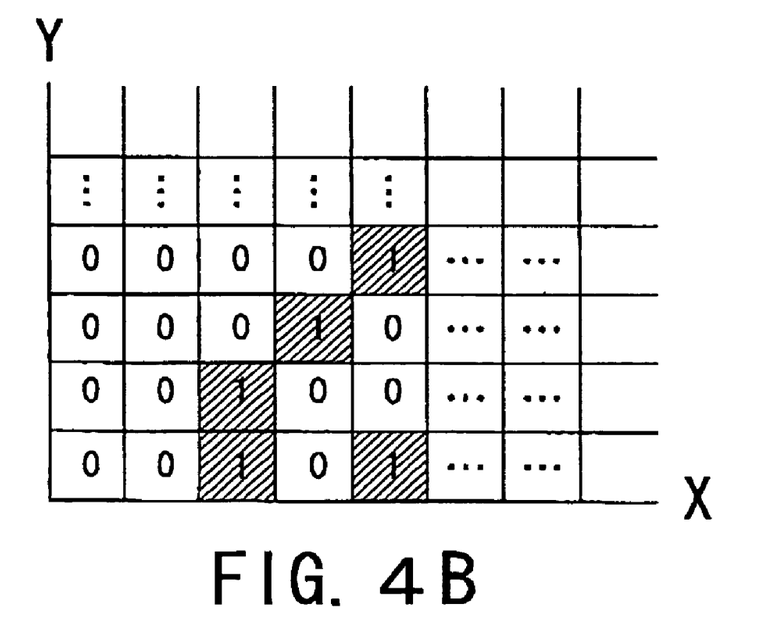
Figure 5:
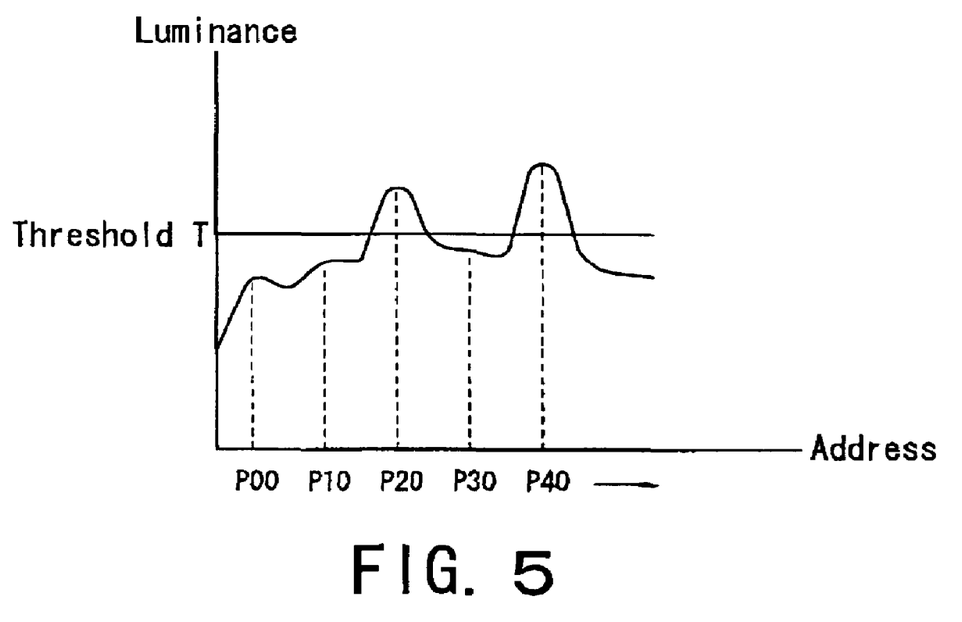
FIG. 5. is a schematic diagram representing an example of luminance in one pixel row.
Figure 6A:
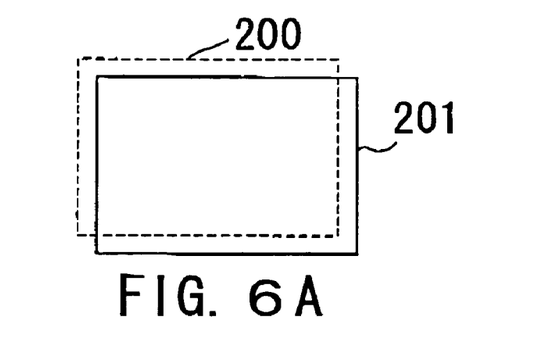
FIGS. 6A to 6D are schematic diagrams showing examples where a digitized present image is superimposed on a digitized standard image.
Figure 6B:
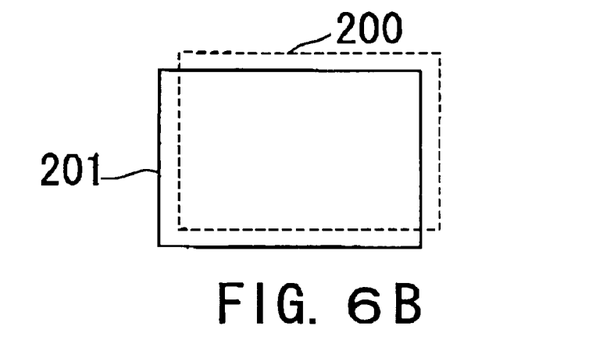
Figure 6C:
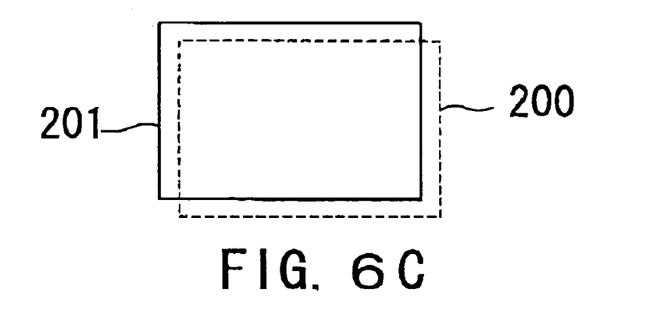
Figure 6D:
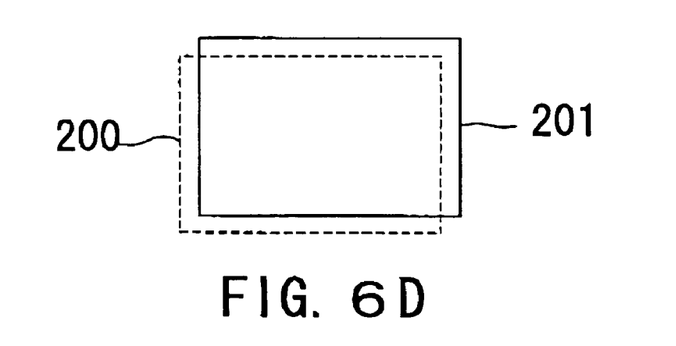

The luminance in the respective pixels varies pixel to pixel as shown in FIG. 5. Hence, the luminance therein is digitized so that a bit is set to 1 (bit 1) in the pixel where the luminance is not lower than a threshold luminance level T, and a bit is set to 0 (bit 0) in the pixel where the luminance is lower than the threshold luminance level T. Thereby, the standard fundus image as shown in FIG. 4A is converted into a digitized standard fundus image consisting of the bits 0 and the bits 1 as shown in FIG. 4B. Also, in the same manner as above, the present fundus image is digitized based on the threshold luminance level T to be converted into a digitized present fundus image. Incidentally, the images are digitized pixel by pixel in the present embodiment; however, they may be digitized by a plurality of pixels as one unit. For example, assume that four adjacent pixels form one unit, and assume that an average value of the respective luminance of the four pixels is the luminance of the four pixels, the whole image may be digitized based on the threshold luminance level T. Besides, the threshold luminance level T may be changed by the switches 44b.

Next, through an AND operation or an OR operation of the digitized standard fundus image and the digitized present fundus image, the calculation and control unit 40 controls to perform a match between matrixes consisting of sets of the bits obtained by the digitization, so that a relative positional difference (deviation) of the digitized present fundus image from the digitized standard fundus image is obtained (STEP 4). FIGS. 6A to 6D are schematic diagrams representing the match between a digitized standard fundus image 200 and a digitized present fundus image 201. For example, as shown in the FIGS. 6A to 6D, the calculation and control unit 40 controls to move the image 201 with respect to the image 200 vertically and horizontally only by a few pixels, and perform the AND or OR operation to find out a positional relationship where bit rows in the images are most corresponding with each other in a portion where the images 200 and 201 overlap each other. Besides, the calculation and control unit 40, which is capable of parallel processing using the CPUs, may control to perform a plurality of the AND operations or OR operations at the same time in overlapping patterns of the images 200 and 201.

Incidentally, in the case of applying the AND operation in obtaining the relative positional difference of the digitized present fundus image from the digitized standard fundus image, a positional relationship is found out where the sum of AND (the number of the bits which are ON (bit 1)) is the largest in the portion where the digitized standard fundus image and the digitized present fundus image overlap each other. Then, from the found positional relationship between the respective digitized fundus images, a two-dimensional positional difference (deviation) of the digitized present fundus image from the digitized standard fundus image is obtained. Also, in the case of applying the OR operation, a positional relationship is found out where the sum of OR (the number of the bits which are ON (bit 1)) is the smallest in the portion where the digitized standard fundus image and the digitized present fundus image overlap each other. Then, from the found positional relationship between the respective digitized fundus images, the two-dimensional positional difference of the digitized present fundus image from the digitized standard fundus image is obtained.

The calculation and control unit 40 controls to transmit the positional difference, which is obtained through the aforementioned AND or OR operation, into the display control part 45 as data for correcting the display position of the present fundus image. The display control part 45 controls to correct the display position of the present fundus image based on the received correction data to display the image on the monitor 43 (STEP 5). Therefore, the present fundus image displayed on the monitor 43 has a positional relationship approximately corresponding with the standard fundus image.

Further, the calculation and control unit 40 controls to erase the standard fundus image from the memory 41, and set the present fundus image displayed on the monitor 43 (the present fundus image compared with the standard fundus image which is erased) as a new standard fundus image for a present fundus image which is to be stored (captured) next (i.e., the present standard image is renewed). The calculation and control unit 40 controls to digitize the present fundus image which is stored (captured) next for making a positional correction to the present fundus image based on the new standard fundus image, and display the present fundus image on the monitor 43. As described above, it is made by frame to set the present fundus image being displayed on the monitor 43 as the standard fundus image for the present fundus image which is to be displayed next on the monitor 43, so that an error, which is caused by a luminance transition over time in the fundus image made by the fluorescer traveling through the blood vessels in the fundus, may be kept to a minimum. Besides, in the present embodiment, the standard fundus image is renewed by frame; however it is not limited thereto and may be renewed every few frames, or every predetermined time.

Incidentally, in the present embodiment, in a case where there is the positional difference between the present fundus image and the standard fundus image in displaying the present fundus image on the monitor 43, the present fundus image is displayed after the display position thereof is corrected so as to correspond approximately with the display position of the standard fundus image. Therefore, it is preferable that respective photo-receiving ranges of the cameras 26 and 32 are made sufficiently larger than a display range of the monitor 43. Besides, in a case where the entire fundus image cannot be displayed on the monitor 43 as a result of the correction to the display position of the present fundus image, the calculation and control unit 40 controls to display the present fundus image as it is without making any correction to the display position thereof. In such a case, the calculation and control unit 40 controls to display an indication on the monitor 43 saying that no correction is made to the display position or the alignment needs to be performed again.

Usually, the fundus image displayed on the monitor is unintentionally moved by eye movement such as eyeball's vibrations, movement of a line of sight, or the like. Therefore, in the present embodiment as described above, the standard fundus image and the present fundus image stored (captured) in the memory are digitized respectively, and through comparison between the respective digitized fundus images, the display position of the present fundus image is corrected by frame so as to correspond approximately with the display position of the standard fundus image, so that the corrected present fundus image is displayed on the monitor. Consequently, even if the eye moves, the display position of the present fundus image on the monitor appears to correspond approximately with the display position of the standard fundus image, and the display position of the present fundus image appears to be fixed, so that the fundus image becomes easy to observe.

Further, in the present embodiment, the entire fundus image is digitized while the blood vessels or the optic papilla are/is not extracted, so that the present invention may be applied to a display of a fundus image for observation by infrared illumination light, where the fluorescer for emphasizing and displaying the blood vessels is not used.

Besides, the fundus image for infrared observation is displayed as a moving image in black and white on the monitor; however it may be displayed as a moving image in color. Another embodiment of the optical system and the control system for the color display is described referring to FIG. 7.

Figure 7:
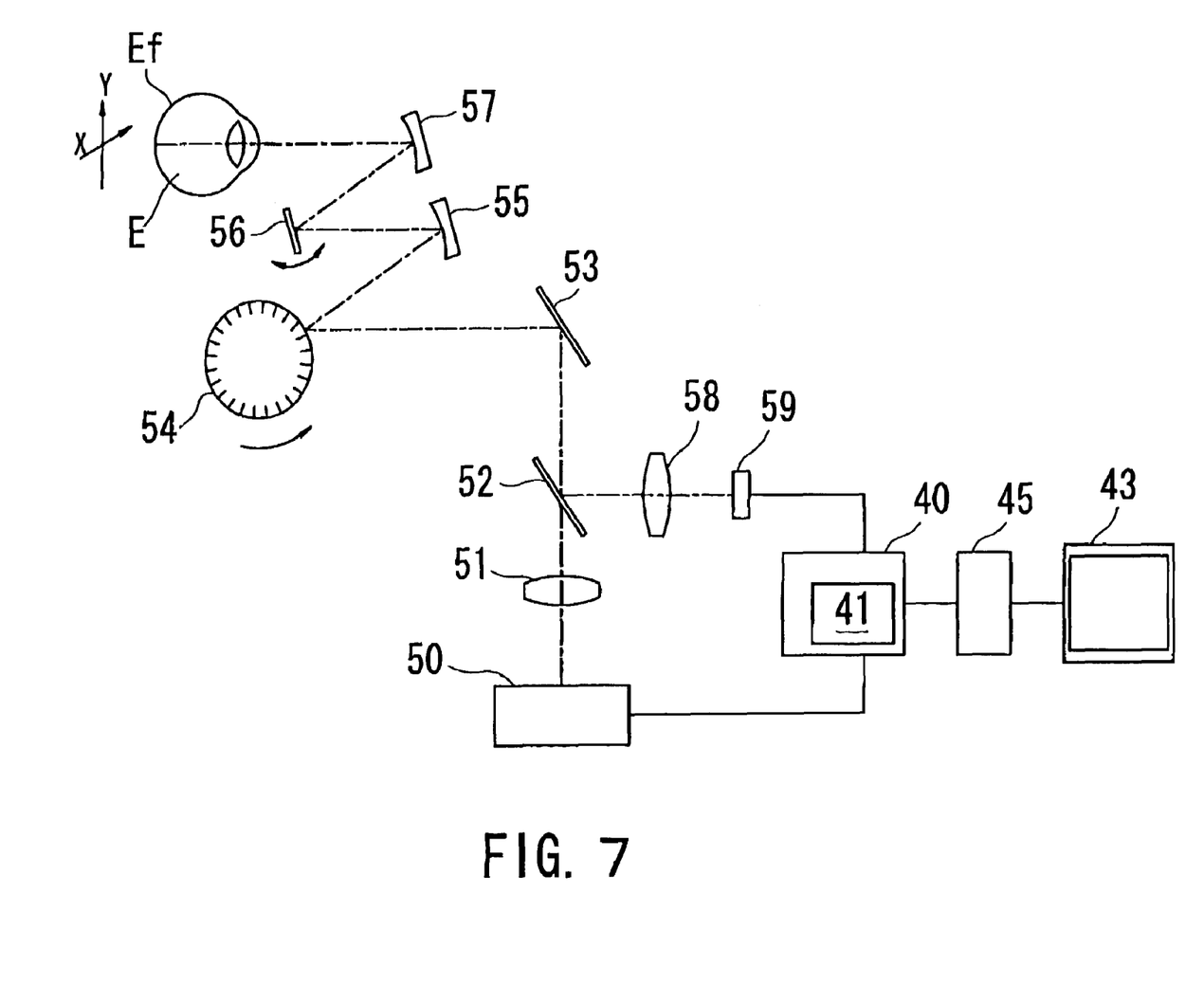
FIG. 7 is a view showing a schematic configuration of a modified embodiment of the optical system and the control system.

An exit unit 50, provided with a light source for independently emitting three-color laser beams in red, green and blue, is capable of switching between the beams in the respective colors in a short period of time, and of irradiating the respective beams. The beam emitted from the exit unit 50 passes through a lens 51, a half mirror 52, a reflection mirror 53, a polygon mirror 54, a concave mirror 55, a galvano-mirror 56 and a concave mirror 57. Then, the beam is scanned on the fundus Ef two-dimensionally (in X- and Y-axis directions) to be irradiated onto the fundus Ef. Besides, the mirror 54 is illustrated such that a rotative direction thereof is the same as that of the mirror 56 for the sake of illustration, but in fact the respective rotative directions are orthogonal to each other.

A reflection beam from the fundus Ef is reflected by the mirror 52 via the mirror 57 to the mirror 53, to be photo-received on a photodetector 59 such as an APD (an avalanche photodiode) via a lens 58. Besides, the photodetector 59 is made to have a positional relationship where the photodetector 59 is approximately conjugate with the fundus Ef with respect to the lens 58.

When the beams in the three colors are independently emitted sequentially from the exit unit 50 and respective fundus images are formed on the photodetector 59, the calculation and control unit 40 controls to store (capture) the respective fundus images once in the memory 41. When all the respective fundus images are stored (captured) in the memory 41, the calculation and control unit 40 controls to digitize the respective fundus images stored (captured) in the memory 41 based on a predetermined threshhold luminance level. Next, the calculation and control unit 40 controls to perform the aforementioned AND or OR operation on the digitized fundus images (for the three colors) to find a positional relationship where the respective fundus images are most corresponding with each other. And from the positional relationship, display-position correction data for the respective fundus images is calculated. When the correction data for the respective digitized fundus images is obtained through the AND or OR operation, the calculation and control unit 40 controls to transmit the correction data into the display control part 45. Based on the received correction data for the respective digitized fundus images, the display control part 45 controls to correct display positions of the respective fundus images, and superimpose the respective fundus images to display on the monitor 43. Consequently, a composite fundus image in color without a positional difference may be displayed on the monitor 43. Also, by determining a standard fundus image as well as performing above-described operations by frame, the fundus image in color may be displayed as a moving image on the monitor while movement of a display on the monitor which is caused by the eye movement is controlled.

Incidentally, the above description has been made taking the fundus camera as an example; however, it is not limited thereto. For example, the present invention may be applied to a variety of apparatuses such as a perimeter for performing examination of a visual field of an eye of an examinee by presenting a test target at an arbitrary position on a fundus while a fundus image for observation is displayed on a monitor.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An apparatus for observing a fundus of an eye of an examinee, the apparatus comprising:
   an image-pickup unit that obtains a fundus image in real time;
   a monitor;
   a display control part that displays the obtained fundus image on a monitor;
   a determination part that determines a standard fundus image based on the displayed fundus image;
   a memory part that stores the determined standard fundus image, and stores a fundus image obtained after the determination of the standard fundus image as a present fundus image every one frame; and
   a calculation part that compares the present fundus image with the standard fundus image two-dimensionally to obtain a positional difference of the present fundus image from the standard fundus image,
   wherein the display control part corrects a display position of the present fundus image so as to have a positional relationship approximately corresponding with the standard fundus image based on the obtained positional difference, and renews the corrected present fundus image every one frame to display on the monitor,
   wherein the determination part determines the present fundus image, which is corrected to be displayed, as a new standard fundus image at predetermined frame intervals, and
   wherein the memory part erases the standard fundus image already stored, and stores the determined new standard fundus image.

2. The apparatus for observing the fundus according to claim 1, wherein the calculation part digitizes the standard fundus image and the present fundus image based on a threshold luminance level to obtain a digitized standard fundus image and a digitized present fundus image, compares the digitized present fundus image with the digitized standard fundus image two-dimensionally, and obtains a difference between corresponding bit rows forming the respective digitized fundus images through one of an AND operation and an OR operation to obtain the positional difference.

3. The apparatus for observing the fundus according to claim 1, wherein the display control part displays the present fundus image without a correction to the display position thereof when the whole present fundus image with a correction to the display position thereof cannot be displayed on the monitor.

4. The apparatus for observing the fundus according to claim 1, the apparatus further comprising:
   an exit unit which emits three-color laser beams in red, green and blue independently; and
   a scanning unit which scans the emitted respective beams on the fundus two-dimensionally, and
   wherein:
      the calculation part digitizes the respective fundus images formed by the respective beams, which are obtained by the image-pickup unit, based on the threshold luminance level to obtain the respective digitized fundus images, and compares the obtained respective digitized fundus images two-dimensionally to obtain positional differences among them, and
      the display control part aligns the respective fundus images based on the obtained positional differences, and superimposes the respective fundus images to be displayed as a composite fundus image on the monitor.

* * * * *